March 22, 1966 H. A. JOHNSON, JR., ETAL Plant Pat. 2,613

STRAWBERRY PLANT

Filed April 21, 1964

INVENTORS
Harold A. Johnson, Jr.
BY Harold E. Thomas
Townsend and Townsend
attorneys United States Patent Office Plant Pat. 2,613

Patented Mar. 22, 1966

2,613

STRAWBERRY PLANT

Harold A. Johnson, Jr., and Harold E. Thomas, Morgan Hill, Calif., assignors to The Strawberry Institute of California, Morgan Hill, Calif.

Filed Apr. 21, 1964, Ser. No. 361,604
1 Claim. (Cl. Plt.—49)

This invention relates to a new and distinct variety of strawberry plant which is the result of a cross between the variety identified as University of California No. 544.3 and the variety identified as Strawberry Institute of California No. C52.3 (both unpatented).

The seedlings resulting from this cross were grown and held in an isolated area near Big Bend, California, and were there asexually reproduced by means of transplanted runners. Testing of these asexually reproduced plants has been carried out in various parts of California.

Figure 1:
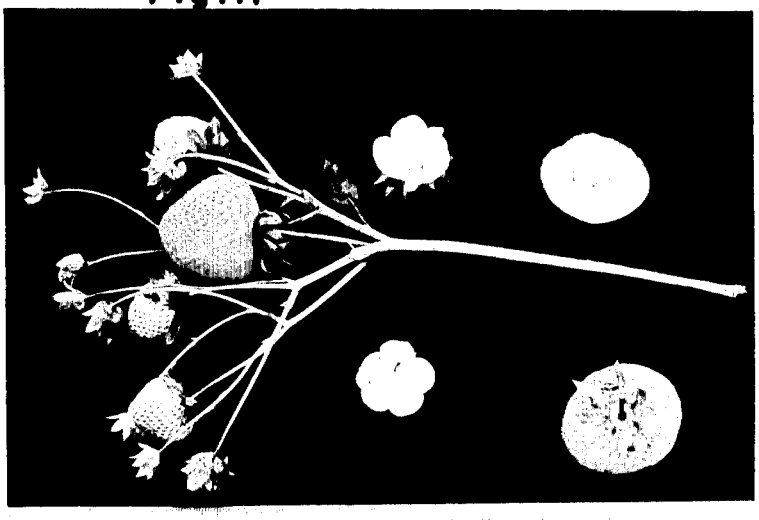
Figure 2:
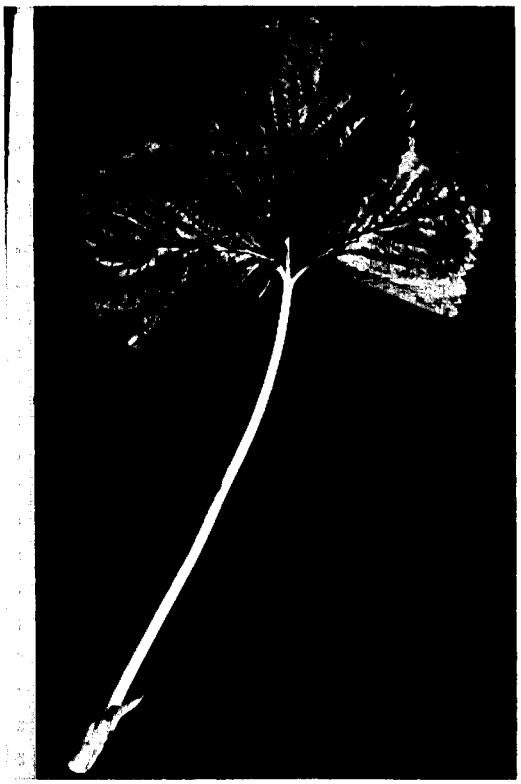

A plant typical of the size, shape and color of the new variety is shown in the accompanying drawing, in which:

FIGURE 1 shows (*a*) a typical flower stem carrying a typical ripe primary and typical green secondary berries, (*b*) a top view and an underview of a typical blossom, (*c*) a view of a typical ripe berry with the calyx attached, and (*d*) a cross section of the berry exhibiting the typical hollow core; and FIGURE 2 shows a typical leaf.

The outstanding characteristic of this new variety is its ruggedness and its ability to grow well when poor or tight soil conditions exist and where solids are moderately alkaline or saline. For example, this new variety is particularly well suited for growth in the Oxnard area of California. It is a rapid-growing variety that becomes dense by the end of the first growing season. The density and vigor of growth of this new variety is about equal to that of the Lassen (unpatented) variety which is widely grown in southern California. Compared to the Goldsmith variety (Plant Patent No. 1,735) this new variety is much more robust and rank in growth.

The plant grows to a medium to large size with a moderately open crown which becomes dense during the second growing season. The foliage of the plant grows in an upright manner and, when grown in a nursery, is of a yellow-green color, lighter than the general overall color of the foliage of the Lassen variety. When grown in the Oxnard area, however, this new variety exhibits foliage of a color generally darker than that of the Lassen variety, but lighter than the foliage color of the Goldsmith variety. The inflorescence of this new variety bears its flowers slightly above the average level of the foliage. The result of this is a long inflorescence that places the fruit well out from the center crown of the plant and makes picking of the fruit relatively easy in that the foliage does not cover and obscure it.

The fruit of this new variety is borne on an inflorescence in much the same way as that of the Lassen variety in that the pedicel of the primary berry and the secondary fruiting stems or the peduncles of secondary berries branch from a common axil on the main fruiting stem or peduncle. The result is a tendency to produce a cluster of berries in a common plane as illustrated in FIGURE 1. The fruit of this new variety when grown under normal conditions has a glossy appearance with a firm, tough skin. These characteristics give the fruit excellent shipping qualities enabling it to arrive at distant markets still maintaining a good appearance. The surface color is very much lighter than that of the Lassen or Goldsmith varieties and tends to be uniform over the surface of the fruit. The shape of the fruit is predominantly wedge conic but may be occasionally conic or round conic. Malformation of the fruit of this new plant may occur early in the season but such malformation is normally less than occurs in the Lassen variety. The size of the primaries and early secondaries is relatively large but slightly smaller than those of the Goldsmith variety grown under similar conditions. As the crop matures, the size of the fruit decreases to medium and occasionally to small. The seed color is bright yellow except on certain exposed surfaces where a reddish tinge prevails.

This new variety tends to produce fruit early in the season unless curtailed by frost. In comparison with the standard varieties of strawberry plants used in southern California, this new variety has been the earliest to produce. In central California it fruits earlier than the Goldsmith variety and more abundantly at the beginning of the season. In the Oxnard area the new variety does well when set in either winter or summer plantings and produces continuously from late February to July and later in some seasons. The new variety may be set out during November or December and will produce the following February to July or later in some seasons. Plants set in summer, i.e. July or August, will produce the following February to July or later in some seasons. But the peak of production is later than the winter set plants.

The dessert quality of the fruit of this new variety is good and is about equal to that of the Goldsmith variety. Because of the high gloss the appearance of the fruit holds well for several days.

This new variety is susceptible to Verticillium wilt. It has not been tested for red stele resistance. Two-spotted mite injures the plant. Its longevity appears good, indicating resistance to virus, but thorough tests have not been completed.

For convenience the characteristics of this new variety of strawberry plant as observed in the Oxnard, California area are summarized as follows:

*Plant characteristics*

*Foliage.*—The foliage is of medium to large size with a moderately open crown during the first growing season and becoming dense in second year. The foliage is mostly directed upward and is higher than Lassen early in growing season. It is of about equal height to Lassen later in the season. The color of the foliage in general is darker than Lassen but lighter than Goldsmith or Shasta and tends to darken as the season progresses.

*Leaves.*—The leaves are relatively large compared to Goldsmith and are thicker and heavier than Lassen. The length is slightly more than the width with the length mostly 7.5 to 10.5 centimeters on first year plants. The surface is mildly rugose with the veins sunken. The serrations are moderately deep and ovate in outline with a moderate point. The leaf blade surface is not flat but tends to regular waves or curls. The color of the upperside of the leaf is Ivy Green as shown on Plate XXXI of Ridgway's Color Standards and Nomenclature (1912 edition). The under side of the leaf is Bice Green as shown on Plate XVII of Ridgeway. The colors are more glossy than the colors of the leaves of the Goldsmith variety.

*Petiole.*—The petioles are medium long but variable, usually in the range of ten to twenty centimeters. They are generally longer than those of Goldsmith. When overgrown the petioles grow much longer than twenty centimeters. They are normally free of bracts. The petiolule of the central leaflet ranges from six to ten millimeters in length in moderate growth and is longer than the petiolule of Lassen.

*Runners.*—The production of runners under nursery conditions is high. Fruiting bed runner production is less than that of Goldsmith.

*Inflorescence.*—The inflorescences are medium long and generally longer than the inflorescences of the Lassen variety. The overall length is generally twenty to twenty-five centimeters, but may be longer. The length of the common peduncle of the fruiting stem is variable but generally longer than that of Lassen. The peduncle holding pedicels of secondary and tertiary fruit join the common peduncle on the main fruiting stem at a single, central peduncle axial, with the pedicel holding the primary berry coming from the axil. This characteristic is also common to the Lassen variety. Bloom is visible above the foliage of the plant. The hair on the tertiary pedicel lays parallel with and is closely appressed to the pedicel and is sparse. The peduncle is thinner than the peduncle of the Goldsmith variety. Normally, but not always, there is a leaf bract of varying size at the axil.

*Fruit characteristics*

*Size.*—The primaries are large in size ranging to fifty millimeters n length on first year plants set in the winter. The size drops off as the crop matures but generally stays within the medium range throughout the crop. In the second fruiting year the size ranges from large to small.

*Shape.*—The shape varies between a conic and a globose conic to wedge or rounded wedge with some tertiaries become globose to oblate as illustrated in the United States Department of Agriculture Bulletin 1043. The rounded wedge shape is in contrast to the shape of the fruit of Goldsmith which has a more distinct and sharper wedge shape. Some of the fruit of this new variety is malformed in early season but such malformation occurs less than in Lassen and other standard varieties under similar conditions.

*Surface.*—The surface is smooth with very few irregularities. The surface gloss is good being better than that of Goldsmith as shown by tests conducted at Oxnard. The surface gloss holds well during shipment.

*Color.*—The color of the fruit is very much lighter than Goldsmith or Lassen. The color is more uniform than Lassen. The color grades from Scarlet Red to Nopal Red, as shown on Plate I of Ridgeway, to pink at the center.

*Core.*—All berries of this new variety have hollow centers with relatively large wedge shaped cavities. The definite core comes out easily with the stem.

*Flesh.*—The skin is relatively firm, approaching the firmness of Goldsmith. The flesh is also firm but less so than the flesh of Goldsmith.

*Seeds.*—The seeds are moderately small in size. They are reddish in color on the exposed surface. Otherwise they are bright yellow. The seeds are positioned even with or slightly above the flesh thus giving protection to the surface. They are mediumly spaced over the fruit surface.

*Flavor.*—The flavor is considered as mild and is subacid and the same generally as Goldsmith, supra. There is no particular aroma to the flesh.

*Calyx.*—The calyx is relatively large but variable in size ranging in diameter from thirty to fifty millimeters. The average number of sepals is ten or more. Sepals are spaced in a single row with a little overlap on large blossoms. The sepal shape alternates between semi-lanceolate and semi-oblanceolate. The apex is mostly pointed with a very few serrated. The calyx is normally irregularly free of the fruit but may become reflexed. It is green and attractive.

The plant above described may vary in slight detail depending upon the climate, the soil and other growth conditions.

We claim:

A new and distinct variety of strawberry plant as herein described and illustrated and characterized particularly by its adaptability to grow well in heavy soils and those of moderate alkalinity or saline content, by its robust growth, vigor and denseness, and by its ability to produce good crops during the first year when winter set.

No references cited.

ABRAHAM G. STONE, *Primary Examiner.*